United States Patent [19]
Klawitter

[11] Patent Number: 5,645,605
[45] Date of Patent: Jul. 8, 1997

[54] IMPLANT DEVICE TO REPLACE THE CARPOMETACARPAL JOINT OF THE HUMAN THUMB

[75] Inventor: Jerome Klawitter, Austin, Tex.

[73] Assignee: Ascension Orthopedics, Inc., Austin, Tex.

[21] Appl. No.: 531,150

[22] Filed: Sep. 18, 1995

[51] Int. Cl.⁶ ............................................ A61F 2/42
[52] U.S. Cl. .................................... 623/21; 623/18
[58] Field of Search ........................ 623/16, 18, 19, 623/20, 21, 22, 23

[56] References Cited

U.S. PATENT DOCUMENTS

| | | | |
|---|---|---|---|
| 4,021,864 | 5/1977 | Waugh | 623/21 |
| 4,131,957 | 1/1979 | Borkos | 3/1.91 |
| 4,231,121 | 11/1980 | Lewis | 3/1.91 |
| 4,242,759 | 1/1981 | White | 623/21 |
| 4,276,660 | 7/1981 | Laure | 3/1.91 |
| 4,459,708 | 7/1984 | Buttazzoni | 623/18 |
| 4,642,122 | 2/1987 | Steffee | 623/21 |
| 4,908,031 | 3/1990 | Frisch | 623/21 |
| 4,955,916 | 9/1990 | Carignan et al. | 623/21 |
| 5,037,440 | 8/1991 | Koenig | 623/21 |
| 5,092,896 | 3/1992 | Meuli et al. | 623/21 |
| 5,405,400 | 4/1995 | Linscheid et al. | 623/21 |

FOREIGN PATENT DOCUMENTS

| | | | |
|---|---|---|---|
| 2670109 | 6/1992 | France | 623/21 |
| 4412721 | 10/1984 | Germany | 623/21 |

*Primary Examiner*—David Isabella
*Attorney, Agent, or Firm*—Fitch, Even, Tabin & Flannery

[57] ABSTRACT

A joint prosthesis designed to replace the carpometacarpal joint of the human thumb. A first element which replaces the articular portion of the first metacarpal mates with a second element which replaces the articular portion of the trapezium. Articulation of the said first and second elements is provided by abutting toroidal mating surfaces which are complementary sections of the surfaces of identical toruses having center hole diameters equal to the diameters of the tubes. Contact of the mating surfaces is only along a pair of curved lines in perpendicular planes providing open spaces for lubrication of the joint by biological fluids.

10 Claims, 4 Drawing Sheets

IMPLANT DEVICE TO REPLACE THE CARPOMETACARPAL JOINT OF THE HUMAN THUMB

FIELD OF THE INVENTION

The present invention relates to a prosthetic device for replacement of the carpometacarpal joint (CMC) of the human thumb.

BACKGROUND OF THE INVENTION

The first elongated bone (metacarpal) at the base of the thumb is connected to the wrist trapezium through the carpometacarpal (CMC) joint which is sometimes referred to as the trapeziometacarpal joint. This particular joint is of critical anatomical importance to humans, due to the opposing motion of the thumb with respect to the fingers for grasping objects and performing daily functions. Damage to the CMC joint through physical injury or disease can therefore be a severe physiological burden to inflicted humans.

Osteoarthritis, rheumatoid arthritis, and post-traumatic arthritis of the carpometacarpal (CMC) joint cause interminable pain and poor function of the thumb. Patients who have mild symptoms often respond to rest, immobilization, non-steroidal anti-inflammatory drugs, or intra-articular injections of steroids. However, patients who have more severe forms of trapeziometacarpal (carpometacarpal) arthritis may have dorsoradial subluxation of the joint, adduction contracture of the first web space, severe loss of articular cartilage, secondary metacarpophalangeal hyperextension and interphalangeal flexion deformity. Carpometacarpal arthritis is often an isolated entity, without significant concomitant involvement of the trapezioscaphoid, trapeziotrapezoid, or trapezium-first metacarpal joint. Moreover, retaining the trapezium in patients who have isolated trapeziometacarpal arthritis is justified in order to preserve stability at the base of the thumb (Lister, et al., "Arthritis of the Trapezial Articulations Treated by Prosthetic Hand", 9:117–129 (1977)). Carpometacarpal total joint replacement can restore the length and direction of the first metacarpal by reducing any existing subluxation of the metacarpal on the trapezium and by providing a fixed fulcrum for the metacarpal to articulate with the trapezium.

The goal of surgical intervention in patients who have CMC arthritis is to restore a strong, painless thumb without deformity or decreased motion. Many reconstructive procedures have been devised including interpositional arthroplasty, resection arthroplasty of the trapezium, resection interpositional arthroplasty of the trapezium, and arthrodesis (see, e.g. Ferrari, B. et al., The Journal of Bone and Joint Surgery, Vol. 68-A:8, 1117–1184 (1986)). Various types of prosthetic joints have been developed for surgical replacement of the metacarpophalangeal and interphalangeal joints of the fingers including the CMC joint of the thumb. Examples of prostheses are shown in the following U.S. Pat. Nos. 5,092,896, issued Mar. 3, 1992; 4,955,916, issued Sep. 11, 1990; 4,276,660, issued Jul. 7, 1981; 4,242, 759, issued Jan. 6, 1981; 4,231,121, issued Nov. 4, 1980; and 3,924,276, issued Dec. 9, 1975. Similar implants have been developed for the toe as described in U.S. Pat. Nos. 5,037, 440, issued Aug. 6, 1991; and 4,908,031, issued Mar. 13, 1990. These patents generally describe joint prostheses having concave and convex bearing areas and variations thereof which tend to be of conventional ball and socket structural design.

Although these aforementioned designs and procedures have been shown to benefit certain patients, none fulfill the requirements of an ideal arthroplasty which restores natural and unaffected thumb use (see, Menon, et al., "The Problem of Trapeziometacarpal Degenerative Arthritis", Arthritis. Clin. Orthop., 175:155–165 (1983)). Therefore, there is a need for a maintenance-free CMC joint replacement which restores to a patient having a damaged or diseased joint pain-free thumb use with natural dexterity and longevity of use.

Accordingly it is the object of the present invention to construct an improved CMC joint prosthesis which allows essentially original and natural function to be restored to the damaged thumb. These and other objects of the invention will be readily apparent from the following detailed description and the accompanying drawings.

SUMMARY OF THE INVENTION

An implant device is provided to replace the carpometacarpal (CMC) joint at the base of the human thumb in the form of a prosthesis composed of two complementary elements or members. One member replaces the articular portion of the first metacarpal bone of the thumb, and the other replaces the articular portion of the trapezium of the wrist. Articulation of the first and second members is formed by abutting toroidal mating surfaces preferably defined by two complementary surfaces that are sections of identical toruses, wherein the center hole diameter of each torus and the diameter of the tube of each torus are the same. The resulting physical contact of the toroidal mating surfaces is very limited, being only generally along two curved lines that are perpendicular to each other, i.e. one lying in a plane which includes the axis of revolution of the torus and being a section of a circumferential ring of the torus tube, and the other lying in the plane which includes the interior circumference of the center hole of the torus. The device with these articulating surfaces mimics the function of the natural joint and minimizes wear and provides joint lubrication in situ because the limited contact provides open regions between the facing surfaces.

DETAILED DESCRIPTION OF PREFERRED EMBODIMENTS

The present invention is directed to a joint prosthesis and to a method for the replacement of a diseased or damaged human joint. The preferred prosthesis is designed for permanent implantation in the human hand.

The thumb of the human hand, owing to its particular opposing position and relative action to the other digits, forms a separate entity without which normal function of the hand is greatly compromised. Most importantly, the thumb is essential for the formation of a grip with each and all of the other fingers and in particular with the index finger. Functionality of the thumb is also essential for numerous other actions of the hand which require a universal-type joint, such as those which place the thumb in the vicinity of the plane of the palm.

Figures 1A, 1B:
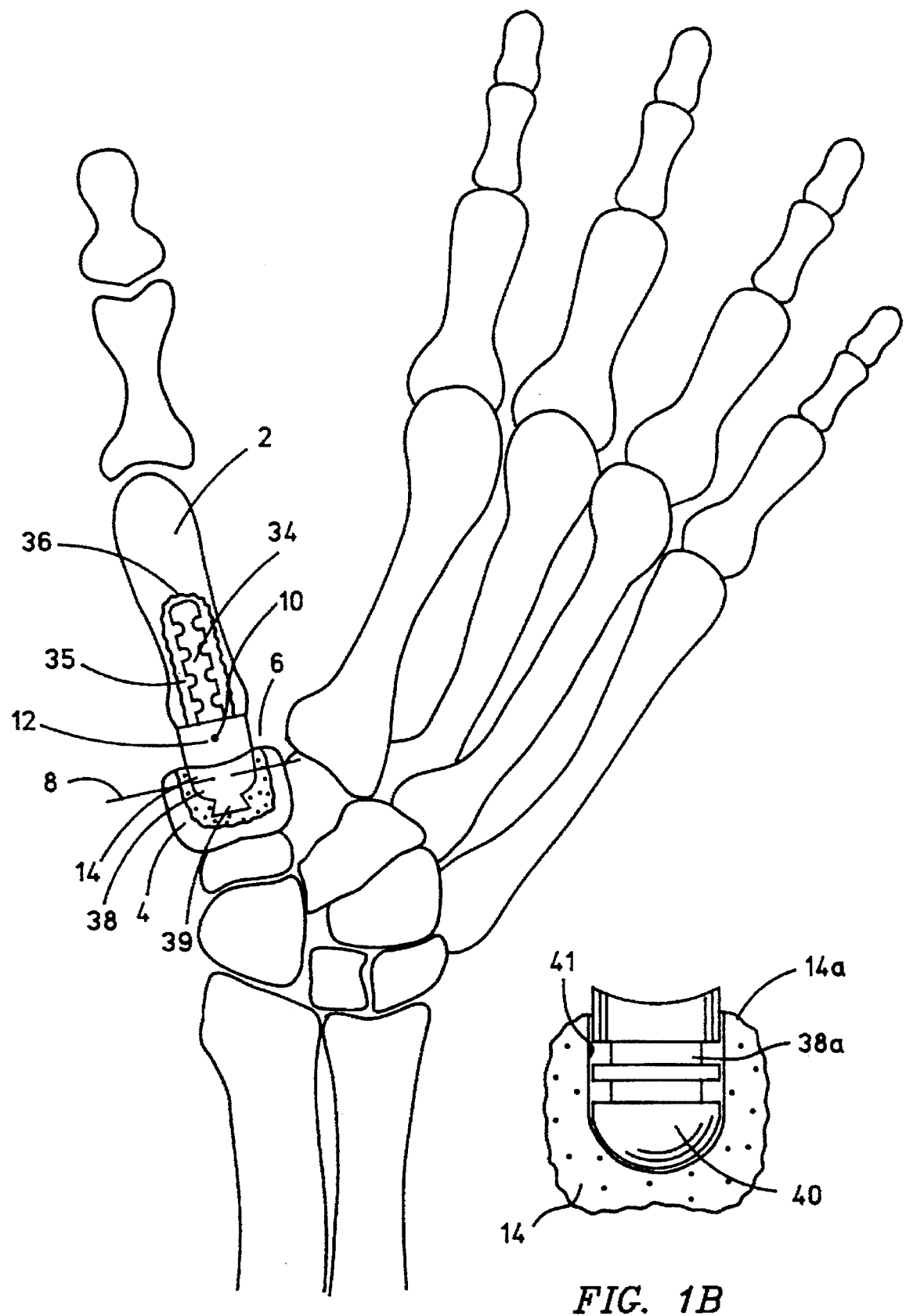
FIG. 1A is a schematic view, partially in section, of the human hand bone anatomy showing an artificial CMC joint embodying various features of the present invention in place therein.
FIG. 1B is a fragmentary enlarged view illustrating an alternative embodiment of the trapezium component of the joint shown in FIG. 1A.

The unique function of the thumb is enabled by the special arrangement of its bony components and associated muscles. As seen in FIG. 1A, the first metacarpal 2 of the thumb is a fairly long bone, which has a hollow tubular shaft. The metacarpal bone has articulating surfaces at each end. A carpometacarpal (CMC) replacement prosthetic joint 6 (also referred to as the trapeziometacarpal joint) is located at the proximal end of the first metacarpal 2 with respect to the wrist, so that the first metacarpal 2 is articulated at the base of the thumb to the wrist trapezium 4 by an implanted prosthetic CMC joint 6.

An axis of rotation between two bones may be defined as a line which does not move in relationship to either bone while they move around each other. The locations of the axes of rotation in the prosthetic CMC joint 6 determine the positions the thumb can take. The CMC joint 6 enables two axes of rotation as shown in FIG. 1A and thereby permits rotary motion in a manner which may be likened to an automotive universal joint. One axis 8 is located in a trapezium element 14 and may lie in the plane of the paper for FIG. 1A. The other axis 10 is located in a first metacarpal element 12; it lies in a plane that is perpendicular to the plane of the paper of FIG. 1A and also to the plane containing the axis 8. One axis is located on each side of the pair of facing articular surfaces that bear against each other and constitute the CMC joint, and the resultant shape of each is generally that of a saddle. Although the articular surfaces of the respective opposing native bones also have a natural saddle shape which enables rotation on each side of the joint, the natural human CMC joint does not have symmetric surfaces, and the axes of rotation are not perpendicular to each other. Movements of flexion and extension of the thumb at the CMC joint occur about the axis 8 passing through the trapezium element 14, i.e. the axis through the center of curvature of the convex surface at the end of the trapezium element. Movements of adduction and abduction of the thumb at the CMC joint occur about the axis 10 passing through the metacarpal element 12. i.e. the axis through the center of curvature of the convex surface of the base or end of the metacarpal element 12.

The CMC prosthetic joint 6, as does the natural joint of the thumb, works by axial compression. i.e., one surface gliding on the other like a pivot. Abduction and adduction occur about a cone whose apex is volar and ulnar to the joint. This allows the metacarpal bone 2 to adopt any position in space whose direction can be altered by the contraction of muscles and ligaments. Articulation of this type, by rotation about the two axes simultaneously, is primarily responsible for the natural accurate positioning of the thumb in opposition to the fingers. The CMC prosthesis 6 of the present invention allows substantially the same spatial motion as did the natural joint.

The prosthesis 6 allows fully functional anatomical articulation between the first metacarpal bone 2 and the wrist trapezium 4 into which the elements 12 and 14 are respectively implanted. The metacarpal element 12 replaces the proximal portion of the first metacarpal bone 2, and the trapezium element 14 replaces the adjacent articular contact portion of the trapezium 4. The two elements mate in such a way as to form a pair of complementary articular surfaces which mimic those of the natural CMC joint. They have unique features which closely emulate the natural ease of motion of the thumb, and the design prolongs the life of the prosthesis by being subject to little wear.

Figure 3:
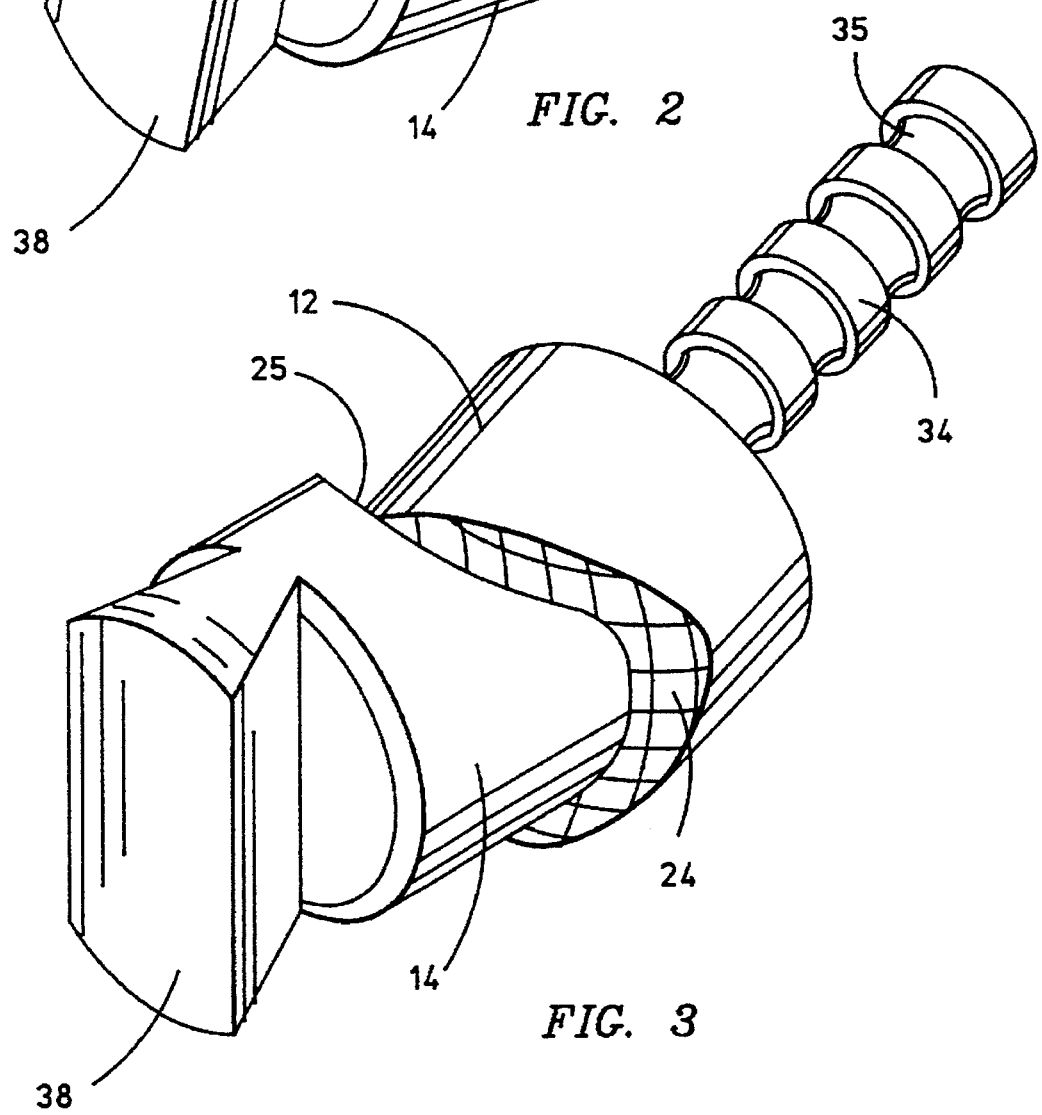
FIG. 3 is a view similar to FIG. 2 which shows the joint in another position of articulation.
Figure 4:
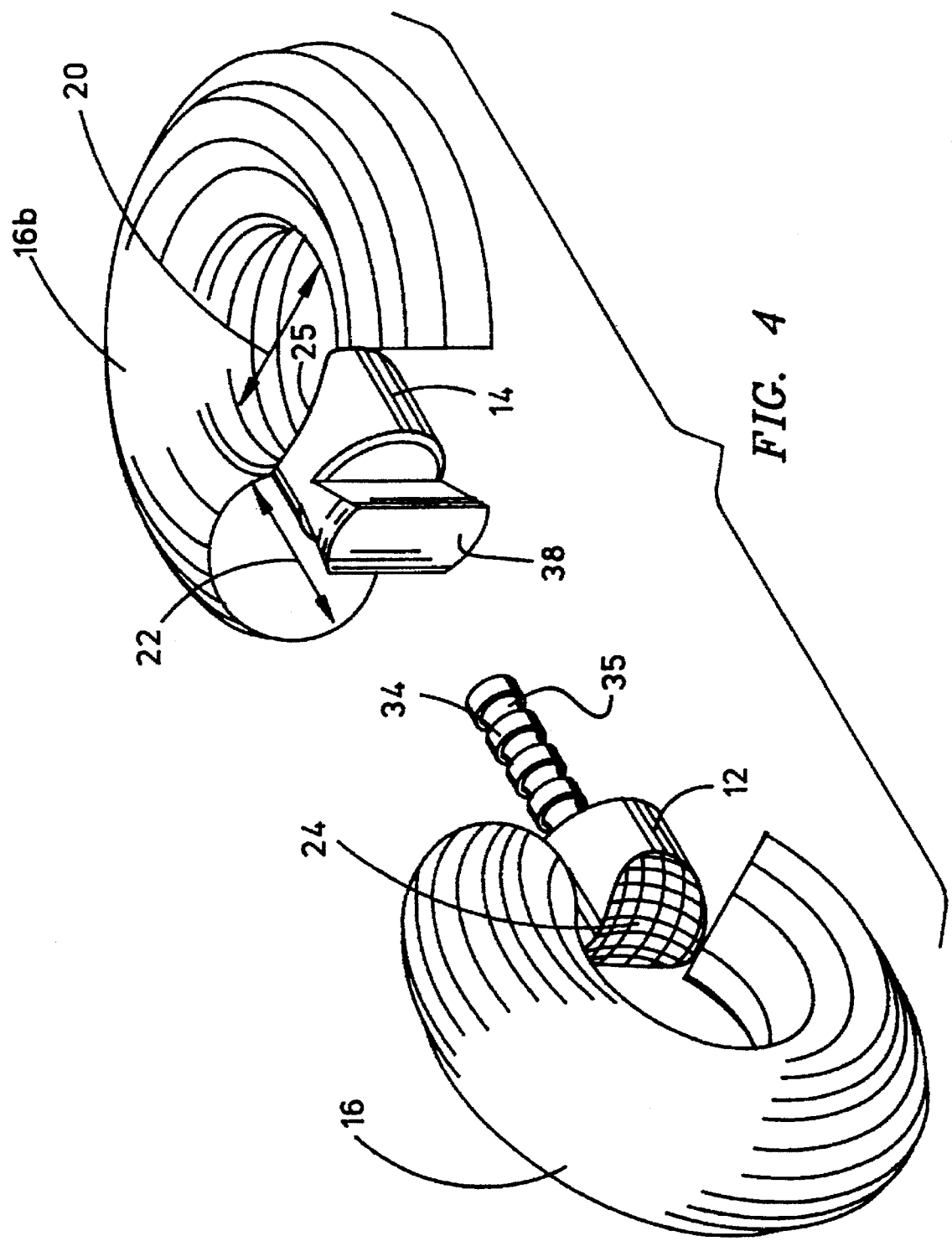
FIG. 4 is a schematic perspective view which illustrates the individual elements of the joint shown in FIGS. 2 and 3 in association with two identical complementary toruses in order to illustrate how the two mating surfaces of the elements are generated, each being a surface portion of an appropriate torus.

Articulating surfaces 24 and 25 of the prosthesis (see FIGS. 2 and 3) are provided at the ends of the metacarpal element 12 and the trapezium element 14, respectively; these surfaces are preferably defined by two complementary sections of surfaces of identical toruses each having a center hole diameter equal to the diameter of the tube, i.e. to the diameter of the circle that is revolved about an axis to generate a torus. FIG. 4 schematically illustrates the relative locations on the toruses from which the toroidal surfaces 24 and 25 are generated. FIG. 4 illustrates two identical toruses 16a and 16b each having a center hole with a diameter 20 equal to the diameter 22 of the circle that is revolved to create the torus. The articulating surfaces 24 and 25 of the elements 12 and 14 are defined by such a two-torus arrangement. By visualizing the tubular portion of one torus located within the center circular opening of the other torus, and vice-versa, it can be seen that there will be contact between the 2 toroidal surfaces only in two perpendicular planes. By preferably intersecting such a composite arrangement with a circular cylinder at a location where the surfaces are in contact with each other, a pair of complementary surfaces 24, 25 are obtained. They may both have the same peripheral outline as would be created by such an intersecting body; although they are preferably circular in their outline or profile, either could have a suitable alternative functional profile if desired.

Figures 5A, 5B, 5C, 5D:
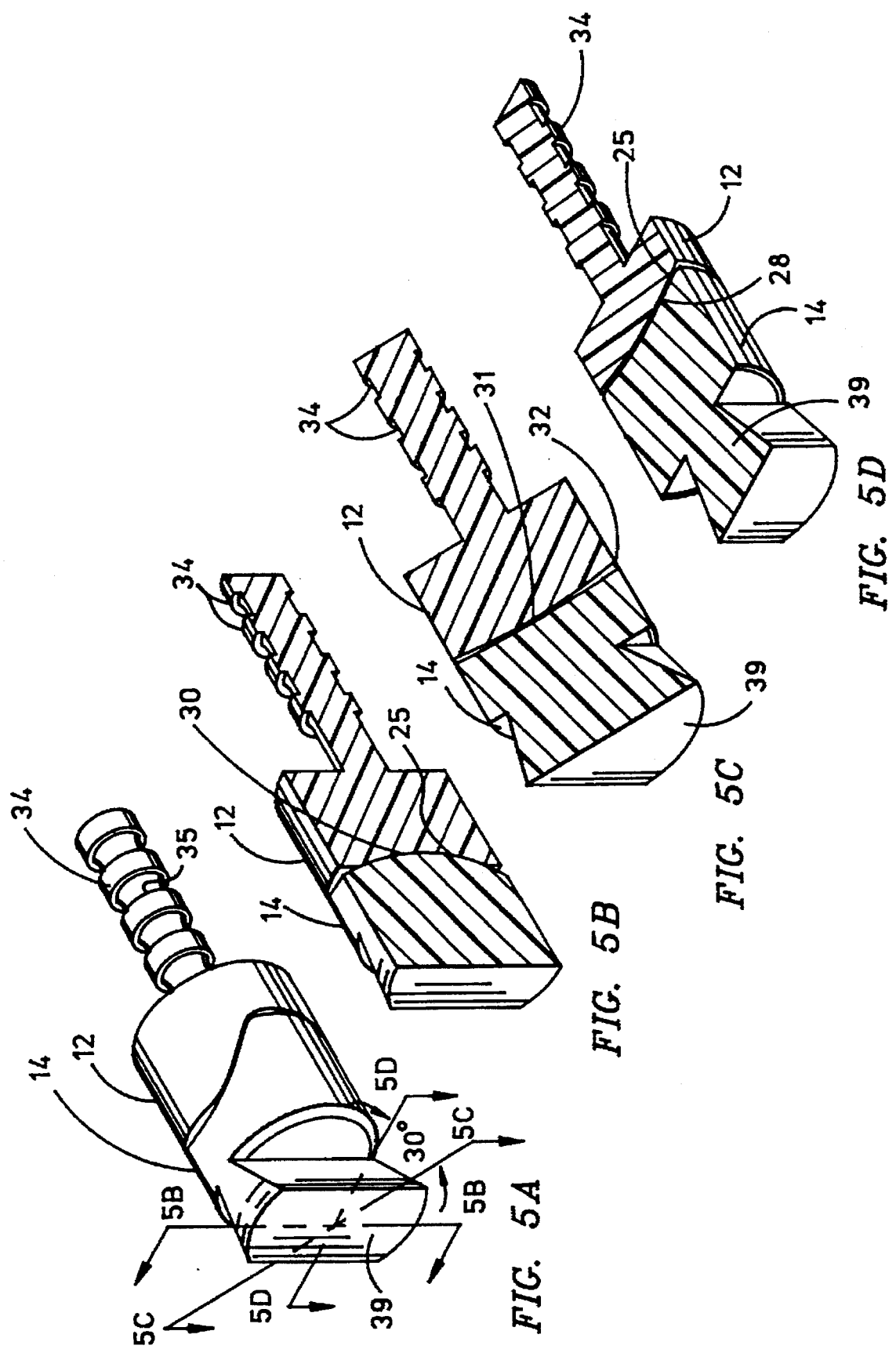
FIG. 5A is a perspective view showing the two elements of FIGS. 2 and 3 in direct longitudinal alignment with each other.
FIGS. 5B–5D are longitudinal sectional views taken along the respective lines 5B—5B, 5C—5C and 5D—5D of FIG. 5A.

In the preferred embodiment, the articulating surfaces 24 and 25 have surfaces that are sections of two identical toruses each having a tube diameter 22 which is the same as the diameter of the center hole 20. Under these conditions the mating articulating surfaces 24 and 25 will contact each other along two curved lines in the vertical and horizontal planes as shown in FIGS. 5B and 5D. Each line of contact is along the interior diameter of one torus and along a circumference of the tube of the other torus. The two lines of contact 28 and 30 lie in the vertical and horizontal planes with the prosthesis in the orientation shown and are perpendicular to each other. The perpendicular, curved lines 28, 30 of physical contact are shown respectively in the horizontal sectional view 5D and in the vertical sectional view FIG. 5B. A sectional view taken along a plane at 30 degrees from the horizontal axis is shown in FIG. 5C and exaggerated somewhat to show that, in such plane and all others except the 0° and 90° planes, there is only a single point of contact 31 located at the center where the two lines 28 and 30 in FIGS. 5D and 5B intersect. As a result, it can be seen that the surfaces 24 and 25 are non-congruent and that open regions between the facing surfaces 24 and 25 provide for the passage of biological fluid for joint lubrication. The elements 12 and 14 are preferably symmetrical about any centerline plane, as shown in FIGS. 5B–5D.

The fact that the articulation is defined by two lines of contact is considered to be important in regard to achieving good wear characteristics in such a prosthetic joint. Sections of linked complementary toruses, which have the common feature of the same tube and center hole diameters, result in bearing surfaces that effectively spread the load across the facing surfaces while still providing open regions for lubrication. This is in contrast to an articulation having point contact or a single line of contact which often result in high wear in a generally similar prosthetic joint.

In addition to having such a characteristic of minimizing wear over a prolonged period, a further important feature of the present joint 6 is one which also is derived from the distinctive mutual contact only along the two perpendicular lines of contact. The available space 32 between two non-congruent surfaces 24 and 25 formed on the mating elements 12, 14, as shown in FIG. 5C, allows biological fluid to enter and thereby lubricate the area of articulation during use. This feature eliminates the condition of a "dry joint" which would have a tendency to result in high friction and wear as well as creating an uncomfortable grinding and/or "squeaky" sensation to the recipient. The facing articulating surfaces 24 and 25 of the metacarpal element 12 and the trapezium element 14 may also be coated with a very thin coating of polyurethane, polyethylene or some other biocompatible polymeric resin to prevent site-specific bone ingrowth and to even further reduce friction, but which would not detract from the non-congruent character of the articular surfaces.

The joint prosthesis elements 12, 14, and particularly the metacarpal element 12, are preferably made of biocompatible materials having a modulus of elasticity in the range of that of natural living bone, e.g. a graphite substrate coated with pyrolytic carbon. However, more importantly, the elements 12, 14 are made of materials having a sufficient hardness such that they will not distend significantly under the normal load to which they will be expected to be subjected during use so that at least about 50% of the open space will remain between the articular surfaces even at full intended load. For the CMC joint, the amount of load to which the two surfaces would be normally subjected is expected to be about 100 pounds. The materials should also exhibit good wear resistance so they will retain their original surface contours following years of implantation. Pyrocarbons meet these criteria, and examples of other suitable materials include biocompatible metal alloys such as chromium-cobalt alloys, e.g. Vitallium®, tantalum, titanium and molybdenum-base alloys, dense metal oxide ceramics such as aluminum oxide and zirconia oxide, and some highly dense, hard polymers. Although both of the elements 12, 14 are preferably made from the same hard biocompatible material, one component might be made from a chromium-cobalt alloy and the other from a hard ultra high molecular weight polyethylene. Most preferably, the elements 12 and 14 are made from pyrolytic carbon having a DPH of at least 200 (Diamond Pyramid Hardness using a 50 gram load) or an equivalent material which would likewise exhibit good wear resistance as a result of such hardness.

The metacarpal element 12 is preferably constructed with an intramedullary stem portion 34 of the CMC joint prosthesis that may be slightly tapered to fit more easily into the long hollow tubular shaft of the metacarpal bone 2 and is provided with a plurality of undercuts and grooves 35 in its outer surface to promote the primary stabilizing ingrowth of bone in these regions. The metacarpal is a long bone having a medullary tubular shaft, and a cavity 36 is prepared by hollowing out this region to accommodate the intramedullary stem 34 of the metacarpal element 12, permitting it to be inserted and anchored in the medullary cavity 36 as shown in FIG. 1. If desired, the intramedullary stem portion 34 may be made of a material different from the portion which defines the surface 24, e.g. from sintered hydroxyapatite, which promotes the formation of bone in such region. The desired medullary cavity 36 is preferably shaped during surgery, using a special broach, to achieve a snug fit with the stem portion 34 of the metacarpal element 12. The intramedullary stem portion 34 of the metacarpal element 12 can be secured within the cavity 36 using one of several methods, such as: 1) bone growth into a porous coating or undulating surface of the intramedullary stem 34, 2) use of bone cement, 3) bonding of the intramedullary stem 34 to the first metacarpal bone 2 by means of a surface-active stem coating such as hydroxyapatite, or 4) a tight mechanical fit of the stem within the medullary cavity 36.

The trapezium 4 is a generally nugget-shaped bone and does not allow for accommodation of a long intramedullary stem. The trapezium element 14 could be attached to the trapezium bone using only an arrangement similar to items 1–4 described supra for the metacarpal element 12. The base 38 of the trapezium element 14 is preferably shaped to interfit with a complementary cavity formed in that specific bone, and actual attachment may be via a multitude of different interengagements such as are known to those skilled in this art. Attachment may be assisted by inter alia, bone cement, tissue ingrowth, bonding to active materials such as hydroxyapatite, mechanical interlocking or a combination of any of these. Irregularities on the surface of the base 38, such as grooves, dimples and undulations, can be used to enhance attachment. The use of a mortise joint configuration at the base 38 of the trapezium is one preferred embodiment for attachment of the trapezium element 14. Special tools and techniques are available to those skilled in this art to cut a proper mortise groove in the trapezium 4 that will receive and snugly mate with a complementary tenon 39 that has been shaped at the base 38 of the trapezium element 14 as shown in FIG. 1A. In another preferred embodiment shown in FIG. 1B, the base 38a of the trapezium element 14a is a hemispherically shaped portion 40 located below a pair of grooves, which base is fit into a similar cup-shaped cavity 41 created in the trapezium 14 using bone cement if desired. Spike-shaped protrusions or interlocking key shapes can also be used to enhance mechanical stability. Very generally standard methods may be used to attach the respective trapezium element 14 and metacarpal element 12 of the prosthetic joint 6 to the trapezium 4 and first metacarpal bone 2 of the thumb (see, e.g. Ferrari, B. et al., The Journal of Bone and joint Surgery, vol. 68-A:8, 1117–1184 (1986)).

Figure 2:
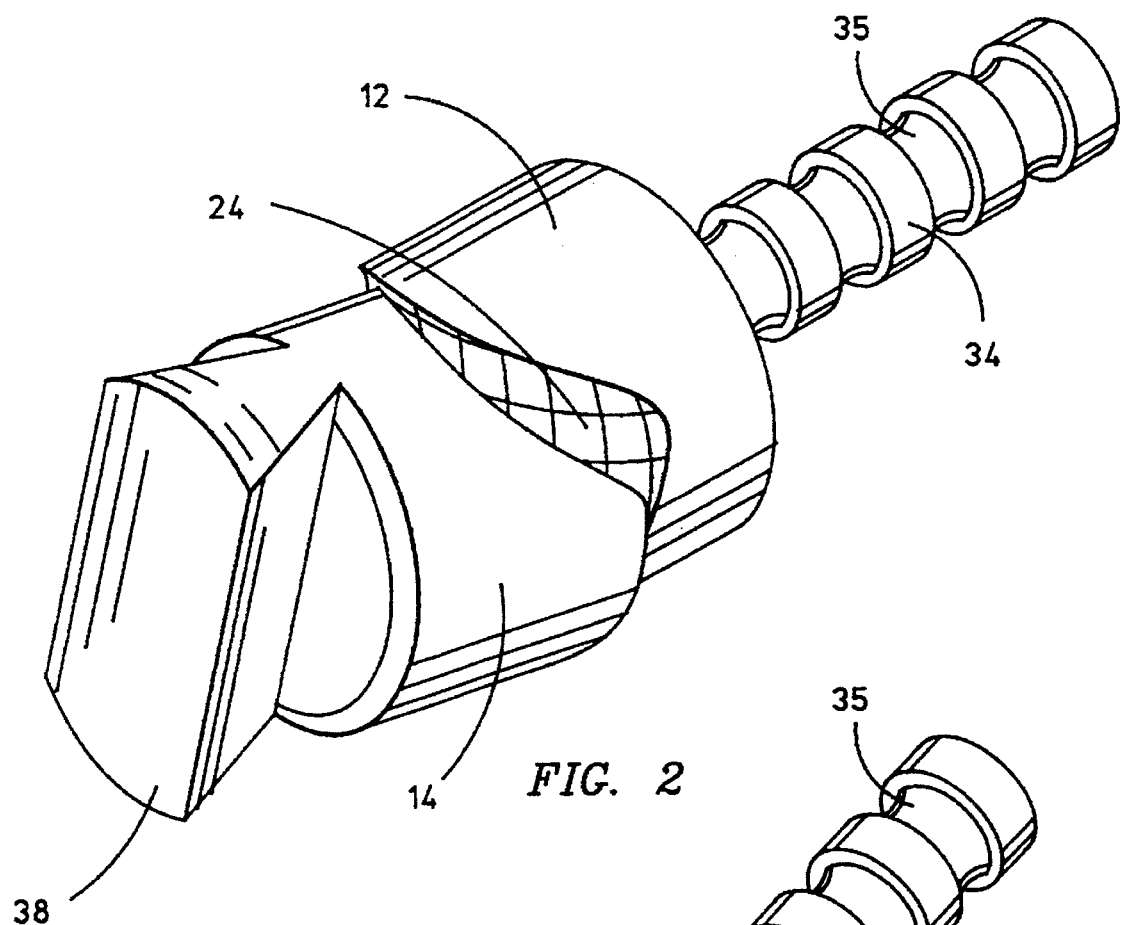
FIG. 2 is a perspective view of the CMC joint of FIG. 1A shown in one position of articulation.

The trapezium element 14 is positioned in the trapezium 4 so that the axis of rotation 8 defined by the curvature of the saddle surface 25 of the trapezium element provides for the desired flexion and extension movements of the thumb, i.e. having the orientation seen in FIG. 1A. This positioning of the trapezium element 14 generally also locates the perpendicular axis of rotation through the curvature of the convex surface 24 of the mating metacarpal element 12, which in turn provides for the adduction and abduction movements of the thumb. As depicted in FIGS. 2 and 3, the prosthetic joint 6 allows compound angular movement between the metacarpal bone 2 and the trapezium bone 4 from the straight-ahead or in-line orientation illustrated in FIG. 1A and in FIG. 5A. In FIG. 2, the displacement of the metacarpal element 12 with respect to the trapezium element 14 is shown as would occur when the angular orientation of the metacarpal bone relative to the trapezium bone is changed in one plane. Starting from this FIG. 2 relative orientation, FIG. 3 illustrates a further sequential displacement of the two elements 12, 14 in a plane perpendicular thereto completing the compound movement. It can be seen that the articular saddle surfaces 24 and 25 accommodate such movement; thus, the prosthetic joint 6 having two such interengaging surfaces of this shape has many advantages.

Although the invention has been described with respect to preferred embodiments, various changes and modifications as would be obvious to one having ordinary skill in the art may be made without departing from the scope of the invention which is defined solely by the appended claims. For example, the articulated prosthetic joint described herein is also contemplated for the replacement of human anatomical joints other than the CMC joint of the thumb.

Particular features of the invention are emphasized in the claims which follow.

I claim:

1. A prosthetic device designed for replacement of the carpometacarpal joint of the human thumb comprising a first element which is shaped to replace the proximal articular portion of the first metacarpal bone and a second element which is shaped to replace the corresponding articular portion of the trapezium, said first and second elements being formed with mating noncongruent articulating surfaces which permit smooth relative angular movement between said first and second elements and each surface is curved to provide matingly surface contact solely along two curved lines of contact, said lines of contact lying in perpendicular planes.

2. A prosthetic device according to claim 1 wherein said mating articulating surfaces are sections of complementary surfaces of toruses, each torus having a central hole of a diameter equal to a diameter of a circle that is revolved to create the torus.

3. A prosthetic device according to claim 1 wherein said elements which are formed with said mating articulating surfaces are made of materials which are sufficiently resistant to deformation to assure that, under normal load upon the joint, said lines of contact between said surfaces remain the same.

4. A prosthetic device according to claim 1 wherein said elements are made of graphite substrates coated with pyrolytic carbon having a hardness of at least about 200 DPH.

5. A method of treating a deteriorated carpometacarpal joint of the human thumb, which method comprises implanting the device according to claim 1 by removing the articular portion of said first metacarpal bone and replacing said removed portion with said first element and by removing the articular portion of said trapezium of the carpometacarpal joint of the human thumb and replacing it with said second element.

6. A joint prothesis designed for implantation in the human body, which comprises a first element having a first end which is shaped to be received within a cavity provided in a first of two articulated human bones and having a mating surface at the other end thereof, a second element having a first end which is shaped to be received within a cavity formed within the other of said two articulated human bones and having a second mating surface formed thereon, and said mating surfaces of said first and second elements being noncongruent and formed to permit smooth relative angular movement between said first and second elements only about two axes which lie in planes that are perpendicular to each other and each surface is curved to provide matingly surface contact solely along two curved lines of contact, said lines of contact lying in perpendicular planes.

7. A prosthetic device according to claim 6 wherein said mating articulating surfaces are sections of complementary surfaces of identical toruses, each torus having a central hole of a diameter equal to a diameter of a circle that is revolved to create the torus.

8. A method of treating a deteriorated carpometacarpal joint of the human thumb, which method comprises removing the proximal articular portion of said metacarpal bone and replacing said removed portion with a first element which is proportioned to replace the proximal articular portion of the first metacarpal bone and which has a first end which is shaped to be received within the intramedullary cavity in said metacarpal bone and which has a surface at the other end thereof for mating with the trapezium, said mating surface being a section of a surface of a torus, which torus has a central hole of a diameter equal to the diameter of the circle that is revolved to create the torus.

9. A method according to claim 8 wherein the articular portion of the trapezium of the carpometacarpal joint is replaced with a second element having a toroidal surface which mates with said mating surface.

10. A method according to claim 9 wherein each said mating surface is a section of an identical torus.

* * * * *